United States Patent [19]

Nishikiori et al.

[11] Patent Number: 5,003,056

[45] Date of Patent: Mar. 26, 1991

[54] ANTIBIOTIC NK86-0279, PROCESS FOR PRODUCTION OF THE SAME AND APPLICATION OF THE SAME

[75] Inventors: Takaaki Nishikiori; Masanori Yamazaki, both of Tokyo; Seiichi Saito, Kashiwa; Nobuyoshi Shimada, Tokyo; Takashi Kurokawa; Kiyonobu Hirose, both of Ageo; Takumi Yamshita, Tokyo; Takako Tsuchiya, Kyoto; Takashi Harada, Tokyo, all of Japan

[73] Assignee: Nippon Kayaku Kabushiki Kaisha, Tokyo, Japan

[21] Appl. No.: 288,786

[22] Filed: Dec. 22, 1988

[30] Foreign Application Priority Data

Dec. 24, 1987 [JP] Japan .................. 62-325459

[51] Int. Cl.$^5$ .............. C12P 1/06; A61K 31/70; A61K 31/71

[52] U.S. Cl. .................. 536/71; 435/886; 435/76; 435/253.5; 536/16.8; 536/14; 536/18.1; 514/27

[58] Field of Search ............ 536/16.8, 18.1, 14, 536/7.1; 514/27; 435/886, 76, 253.5

[56] References Cited

U.S. PATENT DOCUMENTS 4,459,291  7/1984  Shirahata et al. ............ 514/27
4,511,560  4/1985  Tomita et al. ............... 514/27
4,626,503 12/1986  Lee et al. .................. 536/16.8

OTHER PUBLICATIONS

Chem. Abs., vol. 107, 1987, p. 333, Abs. No. 112298n, "Oligomycin E, a New Antitumor Antibiotic Produced by Streptomyces sp. MCI-2225", & J. Antibiot. 1987, 40(7), 1053-7 (Abstract).

Chem. Abs., vol. 96, 1982, p. 292, Abs. No. 65333n, "Trioxacarcins, Novel Antitumor Antibiotics, I. Producing Organism, Fermentation and Biological Activities", & J. Antibiot. 1981, 34(12), 1519-24 (Abstract).

Chem. Abs., vol. 88, 1978, p. 180, Abs. No. 59931z, "Biological Properties of Culture 6734-21 and Conditions for the Isolation of the Antiviral Antibiotic Produced by It", & Antibiotiki (Moscow) 1977, 22(12), 1063-5 (Abstract).

Chem. Abs., vol. 99, 1983, p. 491, Abs. No. 15683g, & JP-A-58 65 293 (Kyowa Hakko Kogyo Co., Ltd.) 18-04-1983.

EP-A-O 058 518 (Merck) (Whole document).

Chem. Abs., vol. 96, 1982, p. 292, Abs. No. 65334p, "Trioxacarcins, Novel Antitumor Antibiotics. II. Isolation, Physicochemical Properties and Mode of Action", & J. Antibiol. 1981, 34(12), 1525-30.

The Journal of Antibiotics, vol. XL, No. 7, pp. 1053-1057.

Primary Examiner—Ronald W. Griffin
Attorney, Agent, or Firm—Henry C. Nields

[57] ABSTRACT

This invention relates to an antibiotic NK86-0279 of the formula:

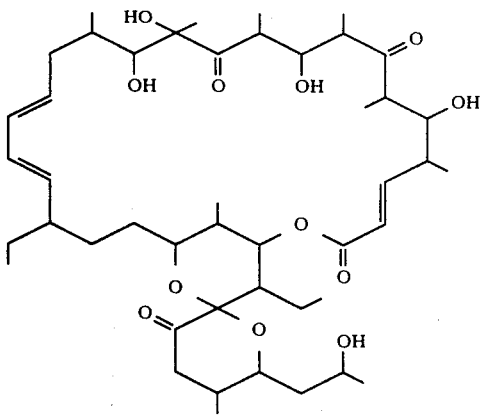

which exhibits antifungal, antitumor, vascularizations-inhibitory and insecticidal activities.

2 Claims, 4 Drawing Sheets

ANTIBIOTIC NK86-0279, PROCESS FOR PRODUCTION OF THE SAME AND APPLICATION OF THE SAME

FIELD OF THE INVENTION

This invention relates to a novel antibiotic NK86-0279, a process for the production of the same and an application of the same.

The compound according to the present invention has antifungal, antitumor and vascularization-inhibitory and insecticidal effects Thus it is expected to be available as agrochemicals such as an insecticide and fungicide or a chemotherapeutic agent against fungi or malignant tumors or in preventing and/or treating diseases caused by vascular neoplasia such as nodose rheumatism, diabetic retinopathy, retinopathy of prematurity, senile macular degeneration or hypercicatrization during the healing of wound.

BACKGROUND OF THE INVENTION

Known antifungal antibiotics include amphotericin B and nystatin A1 while known antitumor antibiotics include cisplatin, bleomycin and adriamycin. In addition, known vascularization inhibitors include indomethacin, medroxyprogesterone, a combination of cortisone and heparin and crude extract of bovine cartilage or aortic wall.

However the occurrence of fungi or cells resistant to conventional antibiotics or antitumor agents has made it necessary to continuously develop novel ones. On the other hand, no vascularization inhibitor so far has been put into practical use as a medicine. Therefore it has been required to develop a novel substance having antifungal, antitumor and vascularization-inhibitory effects.

SUMMARY OF THE INVENTION

Under these circumstances, we have examined various metabolites of microorganisms and consequently found that a strain belonging to the genus Streptomyces produces a novel antibiotic NK86-0279 of the formula (I):

which exhibits antifungal, antitumor, vascularization-inhibitory and insecticidal activity.

The present invention has been completed based on the above finding.

DETAILED DESCRIPTION OF THE INVENTION

The novel antibiotic NK86-0279 as described above can be obtained by culturing an NK86-0279 producing strain belonging to the genus Streptomyces to thereby accumulate NK86-0279 and then recovering the same from the culture medium. A typical example of the NK86-0279 producing strain is *Streptomyces bottropensis* NK86-0279 isolated from soil in Funabashi, Chiba prefecture in August 1986 (FERM BP-1785), deposited at the Fermentation Research Institute Agency of Industrial Science and Technology, 1-3, Higashi 1-chrome Tsukuba-shi Ibaraki-Ken, 305, Japan which will be simply called NK86-0279 strain hereinafter.

The NK86-0279 strain has the following mycological properties.

Mycological properties of NK86-0279 strain:

1. Morphology

When observed under a microscope, this strain shows spiral hyphae from branched aerial hyphae and no whirl. A matured spore chain comprises 20 or more spores (0.6−0.8μ × 1.2−1.4 μ) of a smooth surface. No sporangium is observed.

2. Growth in various media

Each color is expressed according to the standard determined by Nippon Shikisai Kenkyusho.

(1) Sucrose/nitrate agar medium (cultured at 27° C.)

White aerial hyphae are formed on pale yellowish brown vegetative mycelium. A slightly yellowish soluble pigment is observed.

(2) Glucose/asparagine agar medium (cultured at 27° C.)

White to light brownish gray aerial hyphae are formed on pale yellow to pale yellowish brown vegetative mycelium. No soluble pigment is observed.

(3) Starch/inorganic salt agar medium (ISP-medium 4, cultured at 27° C.)

Light brownish gray to brownish gray aerial hyphae are formed on pale yellowish brown vegetative mycelium. A slightly brown soluble pigment is observed.

(4) Tyrosine agar medium (ISP-medium 7, cultured at 27° C.)

Grayish white to light brownish gray aerial hyphae are formed on dark brownish gray vegetative mycelium. A dark brown soluble pigment is observed.

(5) Nutrient agar medium (cultured at 27° C.)

No aerial hypha is formed on pale yellowish brown vegetative mycelium. A slightly brown soluble pigment is observed.

(6) Yeast/malt agar medium (ISP-medium 2, cultured at 27° C.)

Grayish white to brownish gray aerial hyphae are formed on pale yellowish brown vegetative mycelium. A slightly brown soluble pigment is observed.

(7) Oatmeal agar medium (ISP-medium 3, cultured at 27° C.)

Grayish white to light brownish gray aerial hyphae are formed on colorless vegetative mycelium No soluble pigment is observed.

(8) Starch agar medium (cultured at 27° C.)

White to light brownish gray aerial hyphae are formed on pale yellow to pale yellowish brown vegetative mycelium. A lightly brown soluble pigment is observed.

(9) Calcium malate agar medium (cultured at 27° C.)

White aerial hyphae are slightly formed on pale yellow to pale yellowish brown vegetative mycelium. No soluble pigment is observed.

(10) Glycerol/asparagine agar medium (ISP-medium 5, cultured at 27° C.)

Brownish white to light brownish gray aerial hyphae are formed on pale yellow vegetative mycelium. No soluble pigment is observed.

(11) Glycerol/nitrate agar medium (cultured at 27° C.)

White aerial hyphae are formed on pale yellowish brown vegetative mycelium. A slightly brown soluble pigment is observed.

(12) Gelatin stab culture

No aerial hypha is formed on pale yellow to pale yellowish brown vegetative mycelium cultured either in a gelatin medium at 20° C. or in a glucose/peptone gelatin medium at 24° C. A brown soluble pigment is observed.

(13) Skimmed milk (cultured at 32° C.)

White aerial hyphae are formed on pale yellow to pale yellowish brown vegetative mycelium. A brown soluble pigment is observed.

3. Physiological properties (1) Growth temperature range

The test strain is cultured in a yeast/starch agar medium comprising 1.0% of soluble starch, 0.2% of yeast extract (mfd. by NIPPON SEIYAKU CO., LTD.) and 2.0% of agar powder (mfd. by EIKEN CHEMICAL CO., LTD.) (pH 7.0) at 5, 10, 24, 27, 32, 37 and 45° C. As a result, it grows at all of these temperatures except 5 and 45° C. The optimum growth temperature seems to range from 24° to 32° C.

(2) Liquefaction of gelatin

The test strain is cultured in a 15% gelatin medium at 20° C. and in a glucose/peptone/gelatin medium at 27° C. As a result, the liquefaction of the gelatin is observed from the 17th day in each case. Thus the liquefying effect of the test strain on gelatin is relatively low.

(3) Hydrolysis of starch

The test strain is cultured in a starch/inorganic salt agar medium at 27° C. and in a starch agar medium at 27° C. As a result, the hydrolysis of the starch is observed from the 10th day in each case. Thus the hydrolyzing action of the test strain on starch is moderate.

(4) Coagulation/peptonization of skimmed milk

The test strain is cultured in defatted milk at 32° C. As a result neither coagulation nor peptonization of the skimmed milk is observed even on the 21st day.

(5) Formation of melanin-like pigment

The test strain is cultured in a trypton/yeast/broth ISP-medium 1 at 27° C.; in a peptome/yeast/iron agar medium, ISP-medium 6 at 27° C.; and in tyrosine agar medium, ISP-medium 7 at 27° C. As a result, a melanin-like pigment is formed in each case.

(6) Utilization of carbon source

The test strain is cultured in a Pridham-Gottlieb agar medium ISP-medium 6 at 27° C. As a result, it is found that this strain utilizes glucose, L-arabinose, D-xylose, sucrose, inositol, D-fructose, D-mannitol, rhamnose, raffinose and galactose.

(7) Dissolution of calcium malate

The test strain is cultured in a calcium malate agar medium at 27° C. As a result, it exhibits a dissolution effect thereon.

(8) Reduction of nitrate

The test strain is cultured in aqueous peptone containing 0.1% of potassium nitrate ISP-medium 8 at 27° C. The result is negative.

These properties indicate that the NK86-0279 strain belongs to the genus Streptomyces and contains LL-2;6-diaminopimelic acid in the cell wall. It shows spiral aerial hyphae without any sporangium nor whirl. The surface of a spore is smooth. It forms grayish white to light brownish gray aerial hyphae on pale yellow to pale yellowish brown vegetative mycelium in various media. A slightly brown soluble pigment is observed. It forms a melanin-like pigment and exerts a relatively low effect of decomposing protein and a moderate effect of hydrolyzing starch.

A known strain which closely relates to the NK86-0279 strain based on the abovementioned properties is *Streptomyces bottropensis* (cf. International J. Systematic Bacteriol., 19, 410 (1969)). These two strains are completely coincident with each other in, for example, the colors of aerial hyphae on various media, utilization of sugars and formation of a melanin-like pigment. These facts indicate that the NK86-0279 strain belongs to *Streptomyces bottropensis*. Thus it is named *Streptomyces bottropensis* NK86-0279.

The NK86-0279 productivity of the *Streptomyces bottropensis* NK86-0279 to be used in the present invention can be enhanced through various mutagenic techniques commonly employed in the art, such as irradiation with UV light or $^{60}Co$, the use of a mutagenic agent selected from among, for example, nitrogen mustard, nitrous acid, N-methyl-N'-nitro-N-nitrosoguanidine (NTG) and 2-aminopterin, transduction or cell fusion.

The antibiotic NK86-0279 of the present invention may be produced by culturing a microorganism, which belongs to the genus Streptomyces and is capable of producing the antibiotic NK86-0279, in a medium to thereby accumulate said antibiotic in the medium and then recovering the same.

Although the culture may be carried out, as a rule, in the same manner as the one employed in the culture of actinomycetes, submerged culture in a liquid medium is generally advantageous. Any medium may be used therefor so long as it contains nutrient sources to be utilized by the NK86-0279 strain.

As the nutrient sources, those conventionally employed in culturing actinomycetes may be employed. Examples thereof include carbon sources such as glucose, galactose, mannitol, dextrin, starch, starch syrup (hydrolysis of starch by malt), soybean oil and mixtures thereof; and inorganic and organic nitrogen sources such as ammonium chloride, ammonium sulfate, urea, ammonium nitrate, sodium nitrate, peptone, meat extract, yeast extract, dry yeast, corn steep liquor soybean oil cake, oatmeal, casamino acids, bacto soytone, soluble vegetable protein and mixtures thereof. The medium may further contain inorganic salt(s) such as common salt, magnesium sulfate, copper sulfate, zinc sulfate, manganese chloride, calcium carbonate and phosphates, if required. Furthermore it may contain organic material(s) capable of promoting the production of NK86-0279, such as nucleic acids, amino acids and vitamins, as well as inorganic material(s). When considerable foaming is observed during the culture, a vegetable oil such as soybean oil or linseed oil or a petroleum defoaming agent such as Pronal 1 (mfd. by Toho Chemical Industry Co., Ltd.) or Silicone KM-70 (mfd. by The shin-Etsu Chemical Co., Ltd.) may be optionally added to the culture medium. It is preferable to effect the culture at a temperature of 25° to 30° C. under neutral or slightly acidic conditions. The aimed NK86-0279 may be produced and accumulated in a liquid medium after continuing the culture for three to six days in general. When the amount of the product reaches the maximum, the culture is ceased and the mycelia are filtered. From the mycelia thus obtained, the aimed product is isolated and purified.

The isolation and purification of the antibiotic from the mycelia may be carried out in a manner commonly employed for the isolation and purification of a microbial metabolite from mycelia producing the same. Although the NK86-0279 is soluble in organic solvents such as methanol, acetone, ethyl acetate and ethanol, it is hardly soluble in water. Thus it may be purified by a method employed for purifying fat-soluble materials.

Namely, the isolation and purification of the aimed NK86-0279 may be carried out by appropriately combining, for example, extraction with various organic solvents and chromatography with the use of silica gel or Sephadex® LH-20.

For example, the culture medium is filtered to thereby collect the mycelia, which are then extracted with acetone twice The acetone solution is concentrated to dryness in vacuo and the residue is washed with n-hexane.

The brown crude powder thus obtained is dissolved in chloroform and purified by silica gel column chromatography. A chloroform/methanol mixture (50:1) is employed as a developing solvent therefor.

Then active fractions are combined and dried to thereby give a brown powder. This powder is dissolved in a mixture of hexane/acetone (3:2) and purified by silica gel column chromatography again.

A hexane/acetone mixture (3:2) is employed as a developing solvent therefor. The active fractions are combined and concentrated to dryness to thereby give a pale yellow powder.

The obtained powder is dissolved in methanol and chromatogrpahed on a Sepahdex® LH-20 column which has been previously equilibrated with said solvent. Active fractions are Combined and concentrated to dryness to thereby give colorless powder. This powder is dissolved in a mixture of methanol/water and crystallized to give the aimed NK86-0279 in the form of a colorless crystal. The NK86-0279 titers during the culture and in the crude fractions are determined by measuring the growth-inhibitory effect thereof on HeLa $S_3$ cells by the dye exlusion test.

Figure 1:
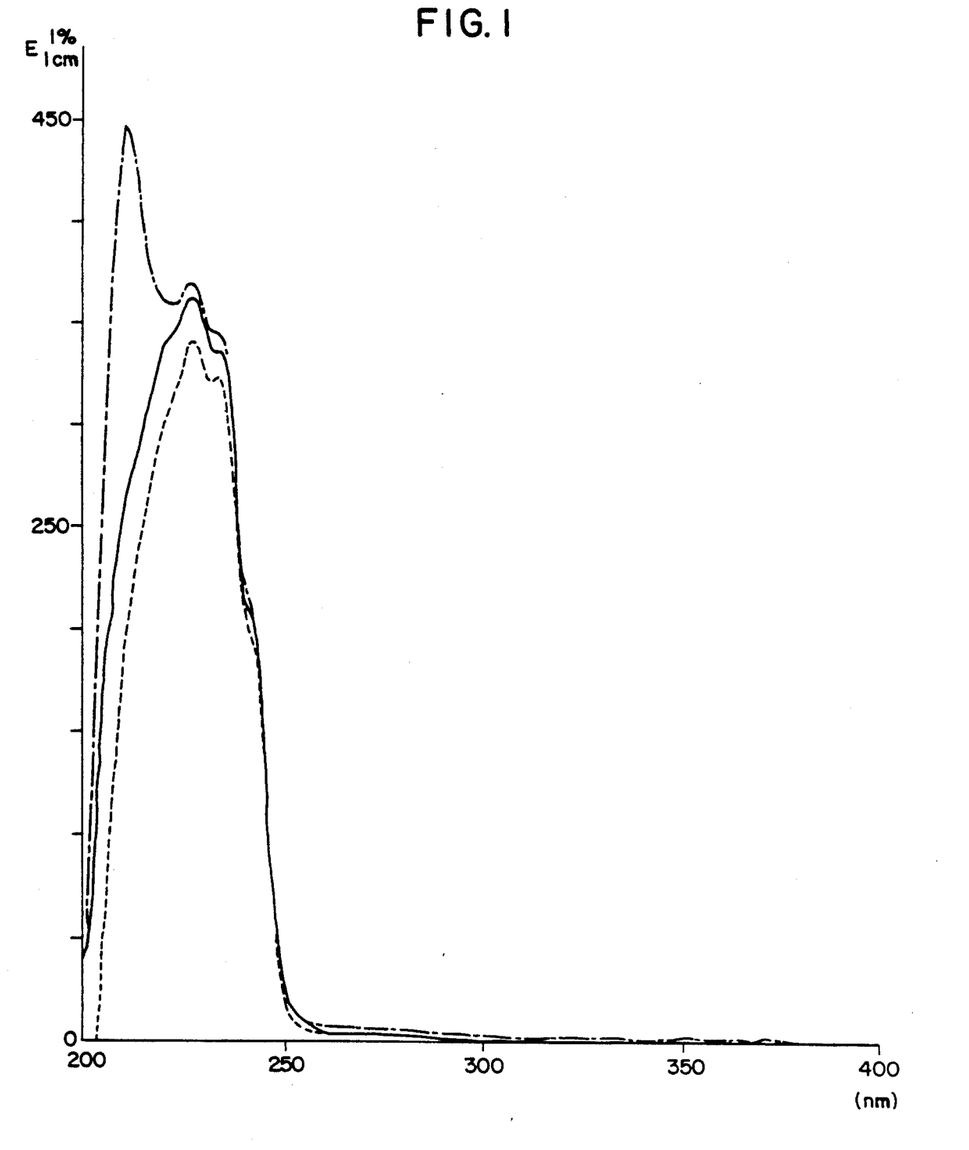
FIG. 1 shows ultraviolet absorption spectra of NK86-0279 wherein ——— represents a 20 μg/ml solution thereof in methanol; ----- represents a 20 μg/ml solution thereof in 0.1 N hydrochloric acid/90% methanol; and ——— represents a 20 μg/ml solution thereof in 0.1 N caustic soda/90% methanol.

The NK86-0279 thus obtained has the following physicochemical properties:
(1) appearance: colorless crystal,
(2) molecular weight: FD-MS m/z; 819 $(M+H)^+$,
(3) elemental analysis: carbon: 66.54%, hydrogen: 9.29% and oxygen: 24.06%,
(4) molecular formula: $C_{46}H_{74}O_{12}$
(5) melting point: 157.0°–159.0° C.
(6) specific rotation: $[\alpha]D\ 20 = -47.0$ (C 1.00, methanol)
(7) solubility: soluble in methanol, acetone, ethyl acetate and dimethyl sulfoxide while hardly soluble in water and hexane;
(8) Rf value in silica gel (Kiesel gel 60 $F_{254}$, 0.25 mm, mfd. by Merck) thin layer chromatography: 0.37 and 0.53 by using developing solvent systems of hexane/acetone (3:2; v/v) and chloroform/methanol (30:1; v/v), respectively,
(9) ultraviolet absorption spectra: as shown in FIG. 1, $$UV\ \lambda_{max}^{methanol}\ (E_{1\ cm}^{1\%}):\ 225.0\ nm\ (364.5),\ 232.5\ nm\ (338.4),\ 242.5\ nm\ (sh.)$$

Figure 2:
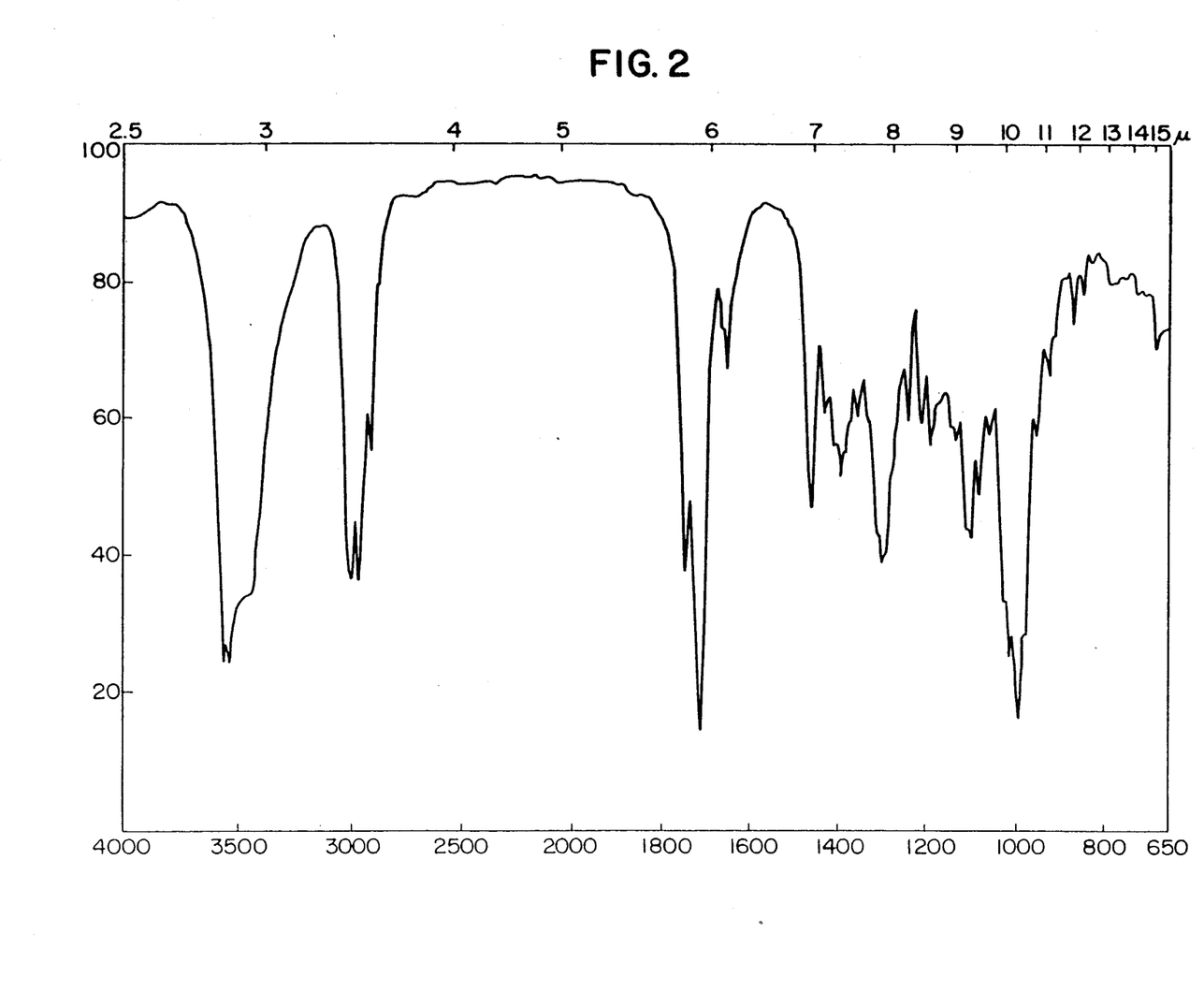
FIG. 2 shows an infrared absorption spectrum of NK86-0279 determined in the form of a potassium bromide tablet.

(10) infrared absorption spectrum (determined in the form of a potassium bromide tablet): as shown in FIG. 2, the absorption maxima (cm$^{-1}$) are as follows:

| | | | | | | | |
|---|---|---|---|---|---|---|---|
| 3525, | 3500, | 3455, | 2955, | 2930, | 2870, | 2340, | 2160, |
| 1920, | 1840, | 1730, | 1700, | 1650, | 1640, | 1450, | 1410, |
| 1395, | 1375, | 1365, | 1345, | 1300, | 1290, | 1270, | 1230, |
| 1200, | 1180, | 1170, | 1125, | 1115, | 1110, | 1100, | 1090, |
| 1070, | 1050, | 1010, | 1005, | 985, | 975, | 950, | 920, |
| 910, | 900, | 880, | 865, | 840, | 820, | 800, | 785, |
| 770, | 745, | 720, | 705, | 675. | | | |

Figure 3:
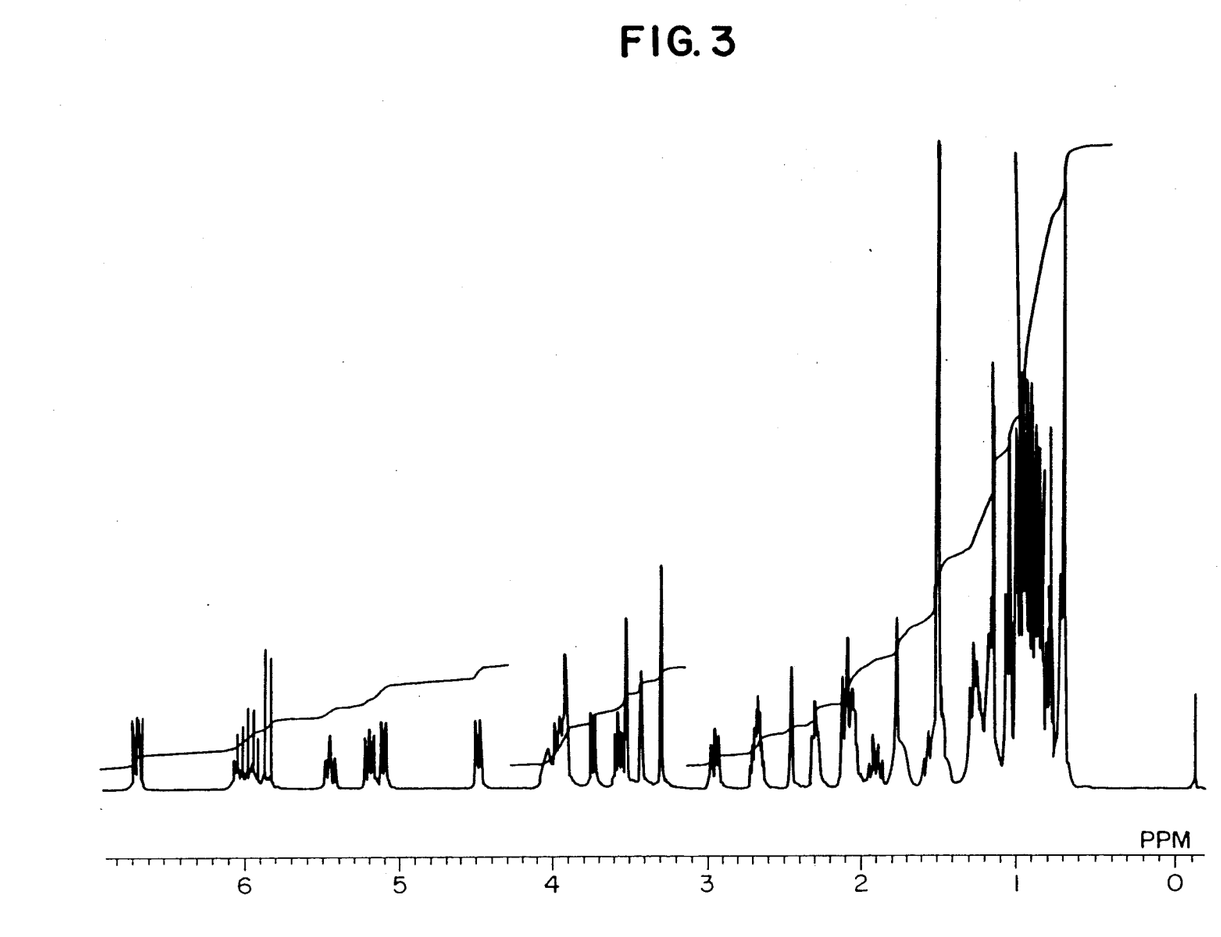
FIG. 3 shows a hydrogen nuclear magnetic resonance spectrum of NK86-0279 determined in deuterated chloroform.
Figure 4:
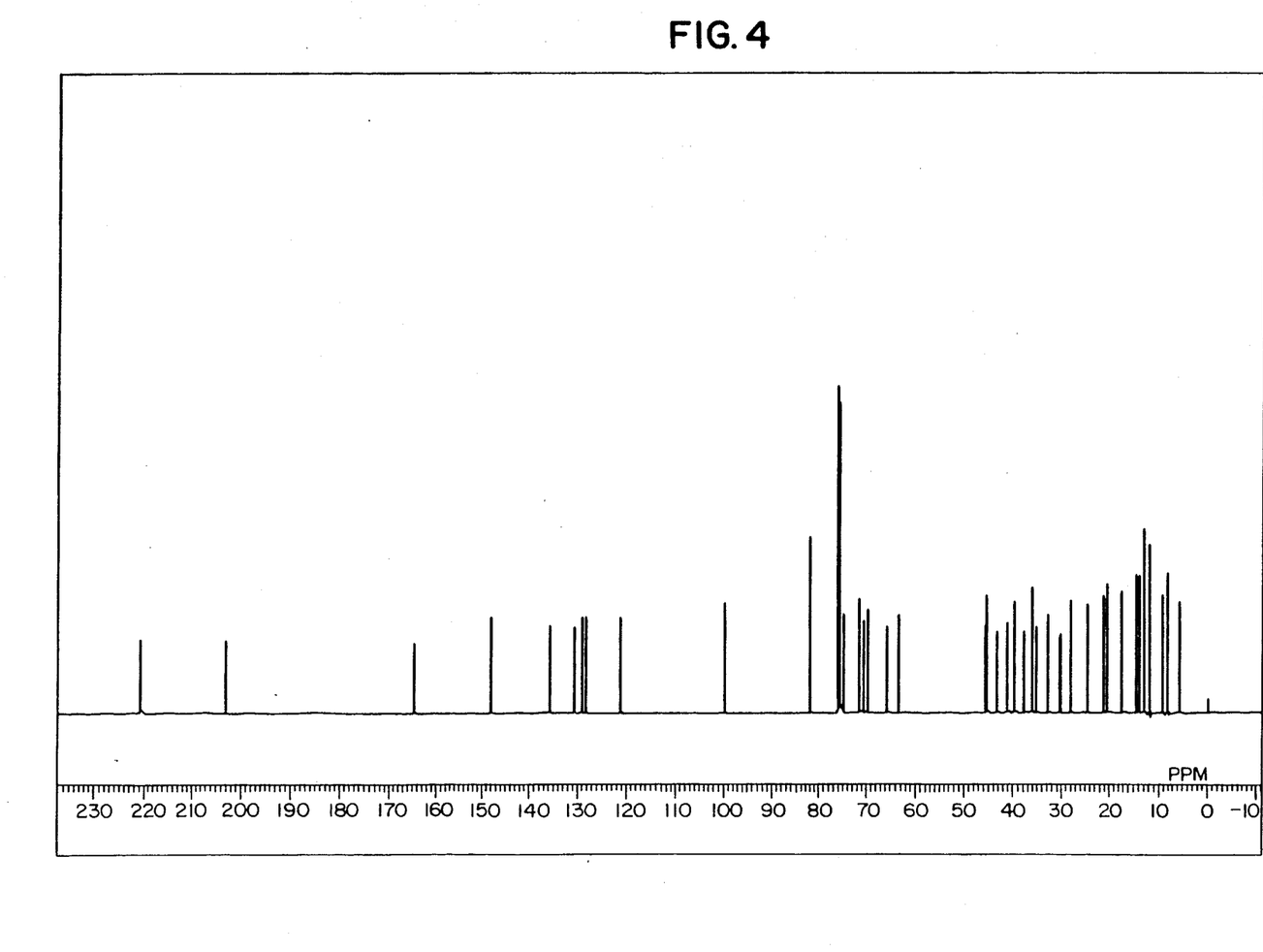
FIG. 4 is a carbon nuclear magnetic resonance spectrum of NK86-0279 determined in deuterated chloroform.

(11) hydrogen unclear magnetic resonance spectrum determined in deuterated chloroform: as shown in FIG. 3,
(12) carbon nuclear magnetic resonance spectrum determined in deuterated chloroform: as shown in FIG. 4, the chemical shift ($\delta$) are as follows:

| | | | | |
|---|---|---|---|---|
| 220.26, | 220.14, | 203.12, | 164.98, | |
| 149.11, | 137.20, | 132.24, | 130.63, | |
| 129.87, | 122.58, | 101.13, | 83.10, | 76.01, |
| 72.99, | 72.67, | 72.04, | 71.02, | |
| 67.10, | 64.60, | 46.60, | 46.14, | |
| 45.96, | 43.95, | 41.87, | 41.74, | |
| 40.34, | 38.38, | 36.79 (x2), | 35.99, | |
| 33.63, | 31.20, | 30.70, | 28.68, | |
| 25.04, | 21.88, | 21.06, | 17.91, | |
| 14.55, | 13.98, | 13.11, | 13.08, | |
| 12.11, | 9.44, | 8.40, | 5.99, | and |

(13) color reactions: positive in molybdatophosphoric acid, sulfuric acid and potassium permanganate reaction while negative in Pauly and Rydon-Smith reactions.

As will be described hereinafter, the compound of the present invention is expected to be useful as a medicine such as antifungal agent, antitumor agent or vascularization inhibitor and as aninsecticide. When the compound of the present invention is to be used for a medicine, it may be either employed alone or mixed with excipient(s) and formulated into, for example, injection, oral drug or suppository. Any pharmaceutically acceptable excipient may be used therefor and the type and composition thereof may be appropriately determined depending on the pathway or method of administration. For example, liquid excipients include water, alchols and vegetable, animal and synthetic oils such as soybean oil, peanut oil, sesami oil and mineral oils, while solid excipients include sugars such as maltose and sucrose, various amino acids, cellulose derivatives such as hydroxypropylcellulose and organic acid salts such as magnesium stearate.

In order to formulate the antibiotic of the present invention into an injection, it is preferable to use excipient(s) such as phyisiological saline solution, various buffers, solutions of sugars, for example, glucose, inositol and mannitol and glycols such as ethyleneglycol and polyethylene glycol. It is also possible to lyophilize the antibiotic of the present invention together with excipient(s) such as sugars, for example, inositol, mannitol, glucose, mannose, maltose and sucrose and amino acids such as phenylalanine. The lyophilized preparation may be dissolved in a solvent suitable for injection, for example, sterilized water, glucose solution, electrolyte solution or amino acid solution and then intravenously or intramuscularly administered.

In order to prepare an oral drug, the antibiotic of the present invention is formulated into various forms such as tablets, capsules, powder, granules, solution or dry syrup together with the abovementioned liquid or solid excipient(s). It is further possible to formulate the same into pellets for endermatic or mucosal administration.

The compound of the present invention may be incorporated into a preparation generally in an amount of 0.001 to 1% by weight, preferably 0.01 to 0.1% by weight. For example, an injection may contain 0.01 to 0.05% by weight of the same, while an oral drug may contain 0.005 to 1% by weight, preferably 0.05 to 0.5% by weight, of the same and the balance of excipient(s).

The dose of the antibiotic of the present invention should be determined depending on the age, body weight and condition of a patient as well as the purpose of the treatment. Generally speaking, it may by administered parenterally at a dose of 0.1 to 5 ug/kg per day, or orally at a dose of 0.5 to 50 ug/kg per day. The acute toxicity ($LD_{50}$) of NK86-0279 on mice is 1.67 mg/kg (i.p.).

When the compound of the present invention is to be used for agrochemicals such as an insecticide or fungicide, it may be employed alone if desired, but they are generally formulated by blending suitable adjuvants to improve or stabilize the effects thereof and used as such or after being diluted if necessary. The compounds of the invention can be formulated in the conventional manners well-known in the art in any convenient form such as dust, granule, micro granule, wettable powder, flowable, emulsion, microcapsule, oil, aerosol, heating fumigant (e.g. mosquito repellent of an incense type or electric type), fuming agent such as fogging, non-heating fumigant, or toxic feed.

Examples of said adjuvants are carrier (i.e. diluent) and other adjuvants such as a spreader, emulsifying agent, wetting agent, dispersing agent, fixing agent or disintegrator.

The content of active ingredients in the formulation of the present invention varies depending on the conditions of use such as formulation form or application method, and is usually from 0.2 to 95% by weight, preferably from 0.5 to 80% by weight, although the active ingredient may be used alone in a special case.

The composition of the present invention may be used in an amount which depends on the conditions such as formulation form, season or method for application. Generally, it is used in an amount of 10 to 300 g/10 a (a = 100 m²), and preferably 15 to 200 g/100 a (in terms of the active ingredient) for the control of insect pests in ornamental forest or livestock and in an amount of 2 to 200 mg/m², preferably 5 to 100 mg/m² (in terms of the active ingredient) for the purpose of exterminating hygienic insect pests. For example, from 15 to 120 g/10 a of the active ingredient is used in the case of dust, 30 to 240 g/10 a thereof is used in the case of granule and 40 to 250 g/10 a thereof is used in the case of emulsion or wettable powder. However, it may be possible, or even necessary, to use the active ingredient in an amount which is outside the range as specified above, in a special case.

Now the effects of the compound of the present invention will be described.

TEST EXAMPLE 1

The antifungal spectrum of the compound of the present invention was examined.

Table 1 shows the antifungal spectrum of NK86-0279 on a Czapek Dox solution agar.

As shown in Table 1, NK86-0279 exerted strong growth-inhibitory effects on fungi including *Penicillium chrysogenum*, *Aspergillus oryzae* and *Torula herbarum*.

TABLE 1

| Test strain | Minimum inhibitory concentration (ug/ml) |
|---|---|
| Mucor javanicus | >100 |
| Aspergillus niger | 6.25 |
| Aspergillus oryzae | 3.13 |
| Penicillium chrysogenum | 1.56 |
| Torula herbarum | 3.13 |
| Botrytis cinerea(*) | 12.5 |
| Fusarium roseum f. sp. | 6.25 |
| Rhizopus hangchao | 6.25 |
| Glomerella cingulata | 6.25 |
| Sporobolomyces salmonicolor | 6.25 |
| Saccharomyces cerevisiae | >100 |
| Candida albicans | >100 |

(*)potato.sucrose agar medium was used.

TEST EXAMPLE 2

The growth-inhibitory effect of the compound of the present invention on HeLa $S_3$ culture cells was examined. A 96-well plate was inoculated with HeLa $S_3$ cells at a ratio of $1.5 \times 10^3$ cells/well and incubated in an incubator at 37° C. under 5% CO for 24 hours. One day after the inoculation, the compound of the present invention was added to the culture medium at various concentrations. Three days after the addition, cells in each well were counted by the dye exclusion method to thereby evaluate the growth-inhibitory effect of the compound of the present invention at various concentrations on HeLa $S_3$ cells.

Table 2 shows the results. Thus the $IC_{50}$ of the compound of the present invention was 0.0027 µg/ml and it exerted a strong growth-inhibitory effect on the HeLa $S_3$ cells.

TABLE 2

| Growth-inhibitory effect of NK86-0279 on HeLa S cells at various concentrations | |
|---|---|
| Concentration of the compound (µg/ml) | Growth-inhibitory ratio (%) |
| 0.00064 | 22.9 |
| 0.0032 | 53.5 |
| 0.016 | 61.2 |
| 0.08 | 73.5 |
| 0.4 | 81.2 |

TEST EXAMPLE 3

3-1

The growth-inhibitory effects of the compound of the present invention on mouse colonic cancer cells (Colon 26) and human colonic cancer cells (SW1116) were examined. A 96-well plate was inoculated with mouse colonic cancer cells at a ratio of $1.5 \times 10^3$ cells per well, while another 96-well plate was inoculated with human colonic cancer cells at a ratio of $3.0 \times 10^3$ per well. These cells were incubated in an incubator at 37° C. under 5% $CO_2$ for 24 hours. Then the compound of the present invention was added thereto at various concentrations. Cells in each well were counted by the dye exclusion method 65 hours and 96 hours after the addition to thereby evaluate the growth-inhibitory effect of the test compound on the mouse colonic cancer cells and that on the human colonic cancer cells.

Table 3-1 shows the results. Thus the $IC_{50}$ of the compound of the present invention on the mouse colonic cancer cells was less than 0.0061 μg/ml, while that on the human colonic cancer cells was 0.021 μg/mlm showing a strong growth-inhibitory effect in each case.

TABLE 3-1

| Conc of the compound (μg/ml) | Growth-inhibitory ratio (%) | |
| --- | --- | --- |
| | mouse colonic cancer cells (Colon 26) | human colonic cancer cells (SW1116) |
| 100 | 103.7 | 90.7 |
| 25 | 108.4 | 91.9 |
| 6.25 | 104.9 | 80.8 |
| 1.56 | 94.2 | 52.2 |
| 0.39 | 87.6 | 53.5 |
| 0.098 | 86.1 | 54.6 |
| 0.024 | 87.5 | 51.7 |
| 0.0061 | 84.6 | 33.3 |

3-2

The anti-cancer action of the compound of the present invention against the cancer of the mouse colon (colon 26) was examined. A cancer debris of mouse colon having an area of 2 mm³ was grafted into a subcutaneous portion of the left body side of a 6 week-old male BALB/c mouse, and the compound of the present invention was intraperitoneally administered to the mouse in various concentrations every day from the next day of the graft once a day for 9 days. The general conditions of the mouse were observed every day after the initiation of the administration. The percentage prolongation of life (T/C) of the mouse with respect to the compound of the present invention was determined from the ratio of the average survival time on the groups of administration of the compound of the present invention relative to that on the control group.

The results are shown in Table 3-2. The compound of the present invention exhibited a maximum percentage prolongation of life of 153% in a group to which the compound of the present invention had been administered in an amount of 0.25 mg/kg, i.e., exhibited a significant antitumor effect as compared with the control group.

TABLE 3-2

| Dose of the compound (mg/kg) | T/C (%) |
| --- | --- |
| 0.000 | 100 |
| 0.063 | 136 |
| 0.125 | 130 |
| 0.250 | 153 |
| 0.500 | 143 |

TEST EXAMPLE 4

4-1

The growth-inhibitory effects of the compound of the present invention on mouse pulmonary cancer cells (LL) and human plumonary cancer cells (PC-3) were examined.

A 96-well plate was inoculated with mouse pulmonary cancer cells at a ratio of $8.0 \times 10^2$ cells per well, while another 96-well plate was inoculated with human pulmonary cancer cells at a ratio of $2.5 \times 10^3$ per well. These cells were incubated in an incubator at 37° C. under 5% $CO_2$ for 24 hours. Then the compound of the present invention was added thereto at various concentrations. Cells in each well were counted by the dye exclusion method three days after the addition to thereby evaluate the growth-inhibitory effect of the test compound on the mouse pulmonary cancer cells (LL) and that on the human pulmonary cancer cells (PC-3).

Table 4-1 shows the results. Thus the $IC_{50}$ of the compound of the present invention on the mouse pulmonary cancer cells was 0.0098 μg/ml, while that on the human pulmonary cancer cells was 2.13 μg/ml, showing a strong growth-inhibitory effect in each case.

TABLE 4-1

| Conc. of the compound (μg/ml) | Growth-inhibitory ratio (%) | |
| --- | --- | --- |
| | mouse pulmonary cancer cells (LL) | human pulmonary cancer cells (PC-3) |
| 100 | 108.6 | 97.2 |
| 25 | 110.5 | 99.3 |
| 6.25 | 113.6 | 85.9 |
| 1.56 | 92.1 | 38.1 |
| 0.098 | 50.0 | 28.0 |
| 0.024 | 30.4 | 25.1 |
| 0.061 | −5.7 | 12.0 |

4-2

The anti-cancer action of the compound of the present invention against mouse lung cancer (lewis lung carcinoma) and mouse breast cancer (Ehrlich B) was examined. $1 \times 10^6$ mouse lung cancer cells or mouse breast cancer cells were grafted into a subcutaneous portion of the groin of an eight week-old male $BDF_1$ or ICR mouse, and the compound of the present invention was intraperitoneally administered to the mouse in various concentrations every day from two days after the graft once a day for 9 days. On the second day after completion of the administration, the minor axis and the major axis of the tumor were measured, and the volume of the tumor was determined by using the following equation: (minor axis)² × (major axis)²/2. Then, the percentage inhibition of proliferation of each tumor with respect to the compound of the present invention was determined from the ratio of the volume of the tumor on the groups of administration of the compound of the present invention relative to that on the control group.

The results are shown in Table 4-2. The compound of the present invention exhibited a maximum percentage inhibition of proliferation of 59.6% in the mouse lung cancer group to which the compound of the present invention had been administered in an amount of 0.5 mg/kg and 67% in the mouse breast cancer group to which the compound of the present invention had been administered in an amount of 0.25 mg/kg, i.e., exhibited an excellent antitumor effect against each tumor.

TABLE 4-2

| Dose of this compound (mg/kg) | Growth-inhibitory ratio (%) mouse pulmonary cancer | mouse breast cancer |
| --- | --- | --- |
| 0.500 | 59.6 | 61.7 |
| 0.250 | 8.9 | 67.0 |
| 0.125 | 57.1 | 44.3 |
| 0.063 | 46.3 | −0.4 |
| 0.032 | — | 22.5 |
| 0.000 | 0.0 | 0.0 |

TEST EXAMPLE 5

5-1

The growth-inhibitory effects of the compound of the present invention on mouse melanoma cells (B16) and human melanoma cells (A375) were examined. A 96-well plate was inoculated with mouse melanoma cells at a ratio of $1.5 \times 10^3$ cells per well, while another 96-well plate was inoculated with human melanoma cells at a ratio of $1.0 \times 10^3$ per wall. These cells were incubated in an incubator at 37° C. under 5% $CO_2$. Then the compound of the present invention was added thereto at various concentrations. Cells in each well were counted by the dye exclusion method 65 hours after the addition to thereby evaluate the growth-inhibitory effect of the test compound on the mouse melanoma cells and that on the human melanoma cells.

Table 5-1 shows the results. Thus the $IC_{50}$ of the compound of the present invention on the mouse melanoma cells was 1.62 μg/ml, while that on the human melanoma cells was 1.87 μg/ml, showing a growth-inhibitory effect in each case.

TABLE 5-1

| Conc. of the compound (μg/ml) | Growth-inhibitory ratio (%) mouse melanoma (B16) | human melanoma (A375) |
| --- | --- | --- |
| 100 | 105.2 | 104.7 |
| 25 | 105.2 | 104.9 |
| 6.25 | 89.7 | 83.6 |
| 1.56 | 48.9 | 44.4 |
| 0.39 | 45.3 | 43.7 |
| 0.098 | 43.1 | 49.4 |
| 0.024 | 36.8 | 39.7 |
| 0.0061 | 5.3 | 19.7 |

5-2: in-vivo test by intraperitoneally administration.

The anti-cancer action of the compound of the present invention against mouse malignant melanoma (B16 melanotic melanoma) was examined $4 \times 10^5$ mouse malignant melanoma cells were inoculated into a subcutaneous portion of the right body side of a 8 week-old male $BDF_1$ mouse, and the compound of the present invention was intraperitoneally administered to the mouse in various concentrations every day from the next day of the inoculation once a day for 10 days. On the 11 days after the inoculation the minor axis and the major axis of the tumor were measured, and the volume of the tumor was determined by using the following equation: (minor axis)$^2$ ×(major axis)$^2$/2 Then, the percentage inhibition of proliferation of each tumor with respect to the compound of the present invention was determined from the ratio of the volume of the tumor on the groups of administration of the compound of the present invention relative to that on the control group.

The results are shown in Table 5-2. The compound of the present invention exhibited a maximum percentage inhibition of proliferation of 80% in a group to which the compound of the present invention had been administered in an amount of 1.0 mg/kg, i.e., exhibited an excellent antitumor effect against the mouse malignant melanoma.

TABLE 5-2

| Dose of this compound (mg/kg) | Growth-inhibitory ratio (%) |
| --- | --- |
| 1.000 | 80.0 |
| 0.577 | 60.4 |
| 0.333 | 53.2 |
| 0.192 | 54.7 |
| 0.111 | 38.4 |
| 0.064 | 40.5 |
| 0.037 | 41.4 |
| 0.021 | 19.3 |
| 0.012 | 50.7 |
| 0.000 | 0.0 |

5-3: in-vivo test by intravenous administration

The anti-cancer action of the compound of the present invention against mouse malignant melanoma (B16 melanotic melanoma) was examined. $5 \times 10^5$ mouse malignant melanoma cells were inoculated into a subcutaneous portion of the right body side of a 6 week-old male C57BL/6 mouse, and the compound of the present invention was intravenously administered to the mouse in various concentrations every day from the next day or from 7 days after the inoculation once a day for 5 days. On the 11 days after the inoculation, the minor axis and the major axis of the tumor were measured, and the volume of the tumor was determined by using the following equation: (minor axis)$^2$ ×(major axis)$^2$/2 Then, the percentage inhibition of proliferation of each tumor with respect to the compound of the present invention was determined from the ratio of the volume of the tumor on the groups of administration of the compound of the present invention relative to that on the control group.

The results are shown in Table 5-3. The compound of the present invention exhibited a maximum percentage inhibition of proliferation of 81.9% in a group to which the compound of the present invention had been administered in an amount of 0.4 mg/kg from 7 days after the inoculation, i.e., exhibited an excellent antitumor effect against the mouse malignant melanoma.

TABLE 5-3

| Dose of this compound (mg/kg) | Growth-inhibitory ratio (%) administered from the next day of the inoculation | administered from 7 days after the inoculation |
| --- | --- | --- |
| 0.40 | 50.5 | 81.9 |
| 0.20 | 56.9 | 76.6 |
| 0.10 | 62.9 | 69.1 |
| 0.05 | 57.0 | 57.4 |
| 0.00 | 0.0 | 0.0 |

5-4: in-vivo test by peroral administration

The anti-cancer action of the compound of the present invention against mouse malignant melanoma (B16 melanotic melanoma) was examined. $5 \times 10^5$ mouse malignant melanoma cells were inoculated into a subcutaneous portion of the right body side of a 6 week-old male C57BL/6 mouse, and the compound of the present invention was perorally administered to the mouse in various concentrations every day from the next day or from 7 days after the inoculation once a day for 5 days. On the 11 days after the inoculation, the minor axis and the major axis of the tumor were measured, and the volume of the tumor was determined by using the following equation: (minor axis)$^2$ ×(major axis)$^2$/2. Then, the percentage inhibition of proliferation of each tumor with respect to the compound of the present invention was determined from the ratio of the volume of the tumor on the groups of administration of the compound of the present invention relative to that on the control group.

The results are shown in Table 5-4. The compound of the present invention exhibited a maximum percentage inhibition of proliferation of 94.6% in a group to which the compound of the present invention had been administered in an amount of 1.0 mg/kg from the next day of the inoculation, i.e., exhibited an excellent antitumor effect against the mouse malignant melanoma.

TABLE 5-4

| Dose of this compound (mg/kg) | Growth-inhibitory ratio (%) | |
|---|---|---|
| | administered from the next day of the inoculation | administered from 7 days after the inoculation |
| 8.0 | 66.0 | 67.0 |
| 4.0 | 64.5 | 75.5 |
| 2.0 | 69.5 | 57.4 |
| 1.0 | 94.6 | 72.3 |
| 0.5 | 90.5 | 44.7 |
| 0.0 | 0.0 | 0.0 |

TEST EXAMPLE 6

The growth-inhibitory effect of the compound of the present invention on endothelial cells was examined. A 96-well plate was inoculated with bovine adrenal capillary endothelial cells at a ratio of 1×10$^4$ cells per well. One day after the inoculation, the compound of the present invention was added thereto at various concentrations. Cells in each well were counted with a Coulter counter three days after the addition to thereby evaluate the growth-inhibitory effect of the test compound on the capillary endothelial cells. Table 6 shows the results Thus the IC$_{50}$ of the compound of the present invention on the endothelial cells was 0.0003 μg/ml, showing a strong growth-inhibitory effect.

TABLE 6

| Growth-inhibitory ratio of NK86-0279 on capillary endothelial cells at various concentrations | |
|---|---|
| Concentration of the compound (μg/ml) | Growth-inhibitory ratio (%) |
| 0.000128 | 35.4 |
| 0.00064 | 63.2 |
| 0.0032 | 78.4 |
| 0.016 | 89.7 |

TEST EXAMPLE 7

The vascularization-inhibitory effect of the compound of the present invention was examined by corneal assay reported by M.A. Gimbrone et al. (J. National Cancer Inst., 52, 413 (1974)). Namely, the center of the cornea of the eye of a rabbit was incised with a knife at a length of approximately 2 mm to thereby form a pouch. Then a slow-releasing pellet containing 100 μg of a crude extract of Ehrlich ascites tumor cells, which had been preliminarily prepared according to a method proposed by R. Langer et al. (Nature, 263, 797 (1979)), was introduced into the pouch. Further another slow-releasing pellet containing 0.3 to 81 μg of the compound of the present invention was introduced thereinto so as to contact these pellets with each other. Then the degree of vascularization was observed four, six, eight and ten days after the introduction. As a result, the vascularization by the Ehrlich ascites tumor cells crude extract was significantly retarded till the fourth day in the groups to which 1 μg or above of the compound of the compound of the present invention had been administered and till the eighth day in the groups to which 1.7 μg or above thereof had been administered, compared with a control group.

TEST EXAMPLE 8

The insecticidal action of the compound of the present invention was examined by the following method.

(1) An imago of two-spoted spider mite acarids (a Kelthane-resistant species) was used as a test vermin, and the mortality rate thereof was assayed according to an ordinary method (described on page 327 of "Noyaku Seibutsu Kenteiho" edited by Toyoji Hosotsuji). Specifically, a solution of the compound of the present invention in acetone (0.1%) was added to 0.5 ml of an aqueous sucrose solution (1%) to have a predetermined concentration. Ten two-spoted spider mite acarids were released in a vessel (200-ml beaker), and the vessel was covered with a paraffin film. The agent solution prepared above was put on the paraffin film, and another paraffin film was put thereon. The beaker was allowed to stand in a thermostatic chamber (20±1° C.) for a predetermined period of time, and the life and death of the test vermin was investigated.

(2) A larva of mosquito culices (a sensitive species) was used as a test vermin, and the mortality rate thereof was assayed according to an ordinary method (described on page 109 of "Noyaku Jikkenho I, Sacchuzaihen" published by Soft Science, Inc.).

Specifically, 10 ml of well water was placed in a vessel (15-ml Schale), and 5 larvae of mosquito culices (the third stage) were released in the vessel. A solution of the compound of the present invention in acetone (0.1%) was added thereto so as to have a predetermined concentration. The vessel was allowed to stand in a thermostatic chamber (26±1° C.) for a predetermined period of time, and the life and death of the test vermin was investigated. The results are shown in Table 8. As is apparent from the Table, the compound of the present invention exhibited acaricidal action and culicidal action.

TABLE 8

| Conc. of the compound (ppm) | Mortality rate (%) | | | |
|---|---|---|---|---|
| | Imagos of two-spotted spider mite after 2 days | Larvae of mosquito after | | |
| | | 2 days | 6 days | 9 days |
| 100 | 100 | — | — | — |
| 10 | 100 | 100 | 100 | 100 |
| 1 | 100 | 0 | 0 | 0 |
| 0 | 0 | 0 | 0 | 0 |

The results suggest that the compound of the present invention exerts antifungal, anticancer, vascularization-inhibitory and insecticidal effects and thus may be highly useful as a novel antifungal agent, antitumor agent vascularization inhibitor or insecticide.

To illustrate a process for the preparation of the compound of the present invention, the following Example will be given.

EXAMPLE 1

100 ml of a medium (pH 7.2) comprising 2% of soluble starch, 0.5% of glucose, 0.5% of peptone, 0.5% of yeast extract, 0.05% of potassium phosphate dibasic, 0.05% of magnesium sulfate and 0.5% of soybean powder was pipetted into an Erlenmeyer flask (500 ml) and sterilized in an autoclave at 120° C. for 20 minutes. Then it was inoculated with one platinum loopful of NK86-0279 strain (FERM BP-1785). The strain was cultured under shaking at 190 rpm at 27° C. in a rotary shaker for two days. Separately 100 ml of a medium (pH 7.0) comprising 4% of glycerol, 0.5% of polypeptone, 0.3% of yeast extract powder, 0.5% of meat extract, 0.3% of sodium chloride and 0.05% of magnesium sulfate was pipetted into a Erlenmeyer flask (500 ml) and sterilized in an autoclave at 120° C. for 20 minutes. Then 2 ml of the abovementioned culture medium was inoculated into the latter flask and cultured therein under shaking at 190 rpm at 27° C. in a rotary shaker for five days. After filtering the culture medium, 3 kg of mycelia were obtained. These mycelia were washed with 3 L of distilled water and 3 L of acetone was added thereto. After stirring overnight, the mixture was extracted. The mycelia were filtered and further extracted with 2 L of acetone. The acetone extract thus obtained (4.8 L) was concentrated to dryness in vacuo to thereby given 5.0 g of a crude extract. 4.2 g of this crude extract was dissolved in chloroform and chromatographed on a silica gel column (400 ml) which had been previously equilibrated with a mixture of chloroform/methanol (50:1), by using said solvent. Active fractions were combined and concentrated to dryness in vacuo to thereby give 122.8 mg of a yellowish white crude powder.

Then this powder was dissolved in a mixture of hexane/acetone (3:2) and chromatographed on a silica gel column (20 ml) which had been previously equilibrated with said solvent. Active fractions were combined and concentrated to dryness in vacuo to thereby give 68.5 mg of a pale yellowish white crude powder.

Then this crude powder was dissolved in methanol and chromatographed on a Sephadex LH-20 column (150 ml) which had been equilibrated with said solvent.

Active fractions were combined and concentrated to dryness in vacuo to give a colorless powder. This powder was dissolved in a mixture of methanol/water and crystallized to give 22.0 mg of the aimed NK86-0279 in the form of a colorless crystal.

We claim:

1. An antibiotic NK86-0279 of the formula:

2. An antifungal agent, an antitumor agent, a vascularization inhibitor or an insecticide comprising an antibiotic NK86-0279 as an active ingredient and excipient.

* * * * *